(12) United States Patent
Whalen et al.

(10) Patent No.: US 6,991,596 B2
(45) Date of Patent: Jan. 31, 2006

(54) ENDOURETHRAL DEVICE AND METHOD

(75) Inventors: Mark J. Whalen, Alexandria, MN (US); Lloyd K. Willard, Miltona, MN (US); John M. Reid, Garfield, MN (US); Mark Baumgartner, Alexandria, MN (US)

(73) Assignee: AbbeyMoor Medical, Inc., Miltona, MN (US)

( * ) Notice: Subject to any disclaimer, the term of this patent is extended or adjusted under 35 U.S.C. 154(b) by 0 days.

(21) Appl. No.: 10/274,027

(22) Filed: Oct. 18, 2002

(65) Prior Publication Data

US 2003/0078467 A1 Apr. 24, 2003

Related U.S. Application Data

(60) Provisional application No. 60/329,859, filed on Oct. 18, 2001.

(51) Int. Cl.
A61F 2/02 (2006.01)
(52) U.S. Cl. .......................................................... 600/30
(58) Field of Classification Search ............ 600/29–31, 600/561, 435, 568–589, 591, 433, 434, 482, 600/483, 485, 486, 505, 507, 560; 128/885, 128/886, DIG. 25; 606/192, 193, 327, 329; 604/915, 919, 920, 327, 329
See application file for complete search history.

(56) References Cited

U.S. PATENT DOCUMENTS

| | | | |
|---|---|---|---|
| 2,078,686 A | 4/1937 | Rowe | 128/255 |
| 2,450,217 A | 9/1948 | Alcorn | 128/350 |
| 2,687,131 A | 8/1954 | Raiche | 128/349 |
| 3,136,316 A | 6/1964 | Beall | 128/350 |
| 3,495,620 A | 2/1970 | Raimondi et al. | 137/529 |
| 3,630,206 A | 12/1971 | Gingold | 128/349 |
| 3,642,004 A | 2/1972 | Osthagen et al. | 128/349 R |
| 3,706,307 A | 12/1972 | Hasson | 128/2 S |
| 3,731,670 A | 5/1973 | Loe | 128/1 R |
| 3,742,960 A | 7/1973 | Dye et al. | 128/349 |
| 3,812,841 A | 5/1974 | Isaacson | 128/1 R |
| 3,908,637 A | 9/1975 | Doroshow | 128/2 F |
| 4,121,572 A | 10/1978 | Krzeminski | 128/2 S |

(Continued)

FOREIGN PATENT DOCUMENTS

WO WO 00/21462 4/2000

OTHER PUBLICATIONS

Vicente, J. et al. *Spiral Urethral Prosthesis as an Alternative to Surgery in High Risk Patients with Benign Prostatic Hyperplasia: Prospective Study.* The Journal of Urology. vol. 142. p. 1504. Copyright 1989.

(Continued)

Primary Examiner—Samuel G. Gilbert
(74) Attorney, Agent, or Firm—Nawrocki, Rooney & Sivertson, P.A.

(57) ABSTRACT

An endourethral device including proximal and distal anchor assemblies selectively spaced apart by a device body is provided. The proximal anchor assembly is adapted to abuttingly engage at least portions of a bladder neck so as to at least proximally anchor said device, the distal anchor assembly being adapted to engage at least portions of a bulbous urethra so as to at least distally anchor said device. The body extends between the proximal and distal anchors assemblies, the device being adapted such that the anchors are selectively spaced apart for fixed positioning within a lower urinary tract in furtherance of a portion of the body at least partially traversing a prostatic urethra.

15 Claims, 7 Drawing Sheets

U.S. PATENT DOCUMENTS

| | | | |
|---|---|---|---|
| 4,217,911 A | 8/1980 | Layton | 128/748 |
| 4,249,536 A | 2/1981 | Vega | 128/349 B |
| 4,301,811 A | 11/1981 | Layton | 128/748 |
| 4,407,301 A | 10/1983 | Streisinger | 128/774 |
| 4,432,757 A | 2/1984 | Davis, Jr. | 604/99 |
| 4,484,585 A | 11/1984 | Baier | 128/748 |
| 4,489,732 A | 12/1984 | Hasson | 128/778 |
| 4,500,313 A | 2/1985 | Young | 604/280 |
| 4,501,580 A | 2/1985 | Glassman | 604/43 |
| 4,538,621 A | 9/1985 | Jarczyn | 128/748 |
| 4,553,533 A | 11/1985 | Leighton | 128/1 R |
| 4,553,959 A | 11/1985 | Hickey et al. | 604/96 |
| 4,612,939 A | 9/1986 | Robertson | 128/774 |
| 4,721,095 A | 1/1988 | Rey et al. | 128/1 R |
| 4,737,147 A | 4/1988 | Ferrando et al. | 604/96 |
| 4,781,677 A | 11/1988 | Wilcox | 604/28 |
| 4,784,647 A | 11/1988 | Gross | 604/178 |
| 4,792,335 A | 12/1988 | Goosen et al. | 604/323 |
| 4,865,030 A | 9/1989 | Polyak | 128/321 |
| 4,865,588 A | 9/1989 | Flinchbaugh | 604/129 |
| 4,873,990 A | 10/1989 | Holmes et al. | 128/748 |
| 4,909,785 A | 3/1990 | Burton et al. | 604/54 |
| 4,932,938 A | 6/1990 | Goldberg et al. | 604/96 |
| 4,932,958 A | 6/1990 | Reddy et al. | 606/192 |
| 4,934,999 A | 6/1990 | Bader | 600/29 |
| 4,946,449 A | 8/1990 | Davis, Jr. | 604/256 |
| 5,030,199 A | 7/1991 | Barwick et al. | 600/29 |
| 5,041,092 A | 8/1991 | Barwick | 604/104 |
| 5,059,169 A | 10/1991 | Zilber | 604/8 |
| 5,071,429 A | 12/1991 | Pinchuk et al. | 606/192 |
| 5,088,980 A | 2/1992 | Leighton | 600/30 |
| 5,090,424 A | 2/1992 | Simon et al. | 128/885 |
| 5,112,306 A | 5/1992 | Burton et al. | 604/101 |
| 5,114,398 A | 5/1992 | Trick et al. | 600/29 |
| 5,140,999 A | 8/1992 | Ardito | 128/885 |
| 5,234,409 A | 8/1993 | Goldberg et al. | 604/96 |
| 5,242,398 A | 9/1993 | Knoll et al. | 604/101 |
| 5,250,029 A | 10/1993 | Lin et al. | 604/96 |
| 5,254,089 A | 10/1993 | Wang | 604/96 |
| 5,271,735 A | 12/1993 | Greenfeld et al. | 604/266 |
| 5,295,979 A | 3/1994 | DeLaurentis et al. | 604/265 |
| 5,320,605 A | 6/1994 | Sahota | 604/101 |
| 5,322,501 A | 6/1994 | Mahmud-Durrani | 604/8 |
| 5,360,402 A | 11/1994 | Conway et al. | 604/97 |
| 5,366,506 A | 11/1994 | Davis | 623/12 |
| 5,380,268 A | 1/1995 | Wheeler | 600/30 |
| 5,385,563 A | 1/1995 | Gross | 604/284 |
| 5,403,280 A | 4/1995 | Wang | 604/96 |
| 5,427,115 A | 6/1995 | Rowland et al. | 128/756 |
| 5,429,620 A | 7/1995 | Davis | 604/283 |
| 5,437,604 A | 8/1995 | Kulisz et al. | 600/30 |
| 5,483,976 A | 1/1996 | McLaughlin et al. | 128/885 |
| 5,512,032 A | 4/1996 | Kulisz et al. | 600/29 |
| 5,527,336 A | 6/1996 | Rosenbluth et al. | 606/192 |
| 5,609,583 A | 3/1997 | Hakki et al. | 604/282 |
| 5,657,764 A | 8/1997 | Coulter et al. | 128/778 |
| 5,707,357 A | 1/1998 | Mikhail et al. | 604/96 |
| 5,711,314 A | 1/1998 | Ardito | 128/885 |
| 5,713,829 A | 2/1998 | Hakky et al. | 600/29 |
| 5,713,877 A | 2/1998 | Davis | 604/246 |
| 5,718,686 A | 2/1998 | Davis | 604/101 |
| 5,724,994 A | 3/1998 | Simon et al. | 128/885 |
| 5,735,831 A | 4/1998 | Johnson et al. | 604/280 |
| 5,752,525 A | 5/1998 | Simon et al. | 128/885 |
| 5,762,599 A | 6/1998 | Sohn | 600/30 |
| 5,766,209 A | 6/1998 | Devonec | 604/8 |
| RE35,849 E | 7/1998 | Soehendra | 604/8 |
| 5,776,081 A | 7/1998 | Kreder | 600/593 |
| 5,785,641 A | 7/1998 | Davis | 600/30 |
| 5,795,288 A * | 8/1998 | Cohen et al. | 600/29 |
| 5,813,974 A | 9/1998 | Guardia | 600/29 |
| 5,846,259 A | 12/1998 | Berthiaume | 606/192 |
| 5,864,961 A | 2/1999 | Vaughan | 33/512 |
| 5,876,417 A | 3/1999 | Devonec et al. | 606/192 |
| 5,884,629 A | 3/1999 | O'Brien | 128/885 |
| 5,916,195 A | 6/1999 | Eshel et al. | 604/96 |
| 5,964,732 A | 10/1999 | Willard | 604/117 |
| 5,971,967 A | 10/1999 | Willard | 604/264 |
| 5,976,068 A | 11/1999 | Hakky et al. | 600/29 |
| 6,004,290 A | 12/1999 | Davis | 604/96 |
| 6,022,312 A | 2/2000 | Chaussy et al. | 600/29 |
| 6,033,413 A | 3/2000 | Mikus et al. | 606/108 |
| 6,056,699 A | 5/2000 | Sohn et al. | 600/561 |
| 6,083,179 A | 7/2000 | Oredsson | 600/587 |
| 6,102,848 A | 8/2000 | Porter | 600/29 |
| 6,105,580 A | 8/2000 | Von Iderstein et al. | 128/885 |
| 6,119,697 A * | 9/2000 | Engel et al. | 128/885 |
| 6,132,365 A | 10/2000 | Sigurdsson | 600/29 |
| 6,167,886 B1 | 1/2001 | Engel et al. | 128/885 |
| 6,193,646 B1 | 2/2001 | Kulisz et al. | 600/29 |
| 6,221,060 B1 | 4/2001 | Willard | 604/264 |
| 6,234,956 B1 | 5/2001 | He et al. | 600/30 |
| 6,447,462 B1 | 9/2002 | Wallace et al. | 600/561 |
| 6,494,848 B1 | 12/2002 | Sommercorn et al. | 600/587 |
| 6,494,879 B2 | 12/2002 | Lennox et al. | 606/8 |
| 6,527,702 B2 | 3/2003 | Whalen et al. | 600/30 |
| 6,569,078 B2 | 5/2003 | Ishikawa et al. | 600/9 |

OTHER PUBLICATIONS

Fabian, K. M. *Der interprostatische "partielle Katheter"*. Urologe. vol. 23. pp. 229-233. 1984.

Fabian, K. M. *Der Intraprostatische "Partielle Katheter"*. Urologe. 1980.

* cited by examiner

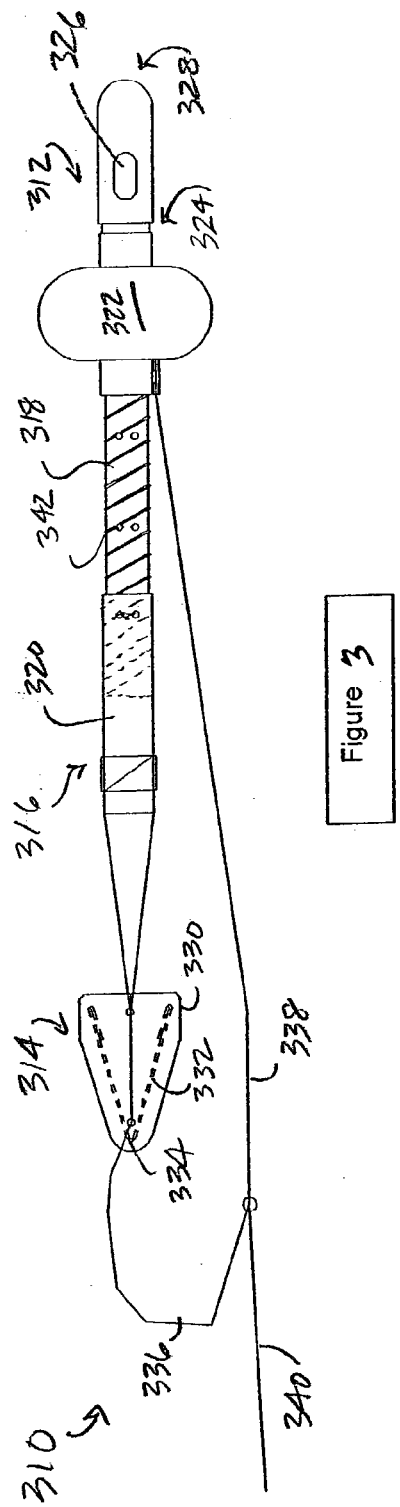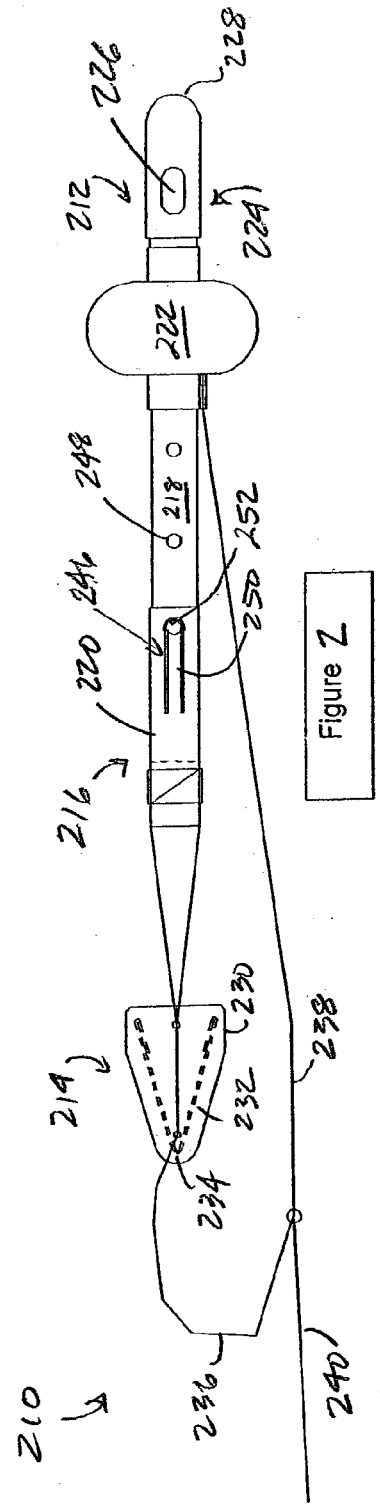

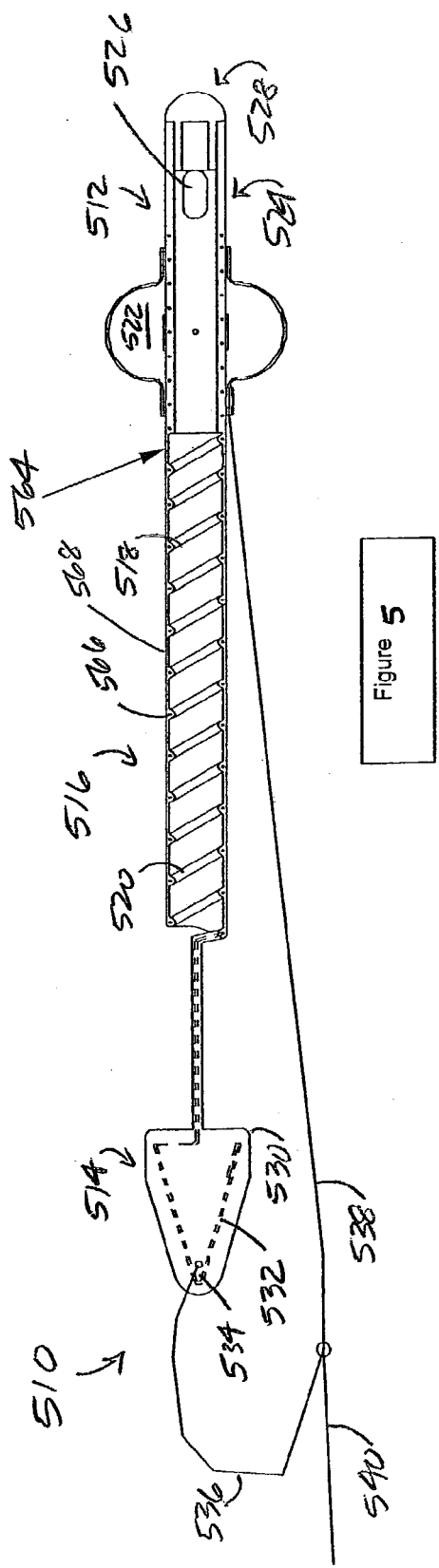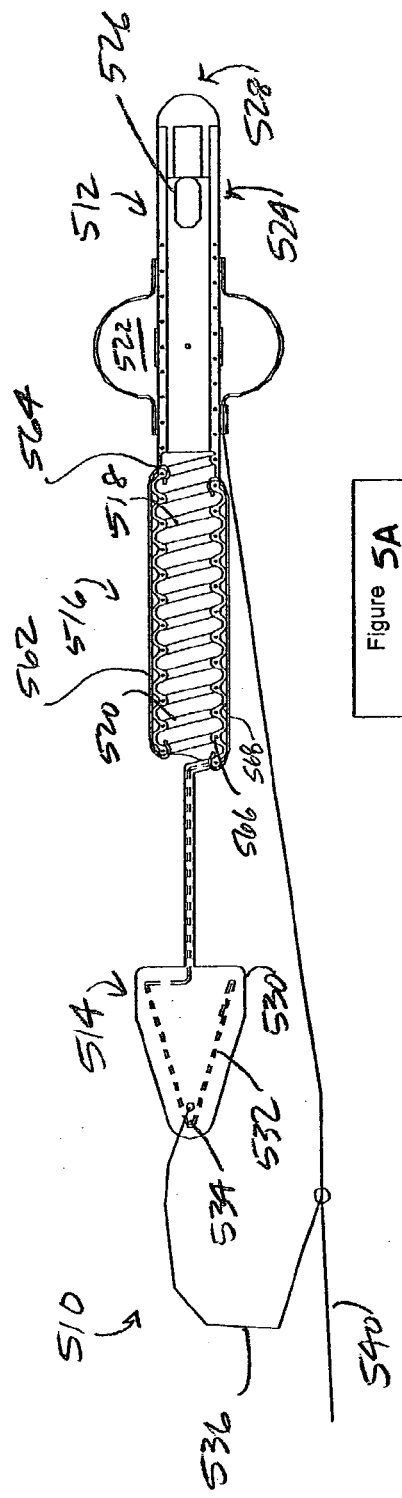

ENDOURETHRAL DEVICE AND METHOD

This is a regular application filed under 35 U.S.C. §111(a) claiming priority under 35 U.S.C. §119(e) (1), of provisional application Ser. No. 60/329,859 having a filing date of Oct. 18, 2001, filed under 35 U.S.C. §111(b).

TECHNICAL FIELD

The present invention generally relates to medical devices, more particularly to endourethral devices, and still more particularly to adjustable length devices for treating urinary retention and or assessing lower urinary tract symptoms.

BACKGROUND OF THE INVENTION

Urinary problems can have serious consequences, particularly when the problem is one of retention or incomplete emptying. Urine flow problems include urine retention, incontinence, and difficult urination. Retention can result from any of a number of causes, including without limitation, spinal cord injury, typhoid, peritonitis, prostatic enlargement, urethral stricture, urethritis, cystitis, bladder tumors, or urethral calculus. Patients suffering from these and other conditions often require some interventional means to periodically drain or augment drainage of the bladder. Failure to do so can result in damage of the epithelium and detrusor muscles associated with the bladder, and an increased potential for bacterial invasion which is commonly thought to contribute to urinary tract infection potentially leading to life-threatening kidney failure.

Beyond notions of intervention, in roads are presently being made in the area of office and office/home based monitoring of patients for purpose of diagnosing the contribution of the prostatic urethra to the outflow urodynamics. Differential diagnosis is understood by accepting that there are three primary anatomical organs which interact to contribute to the function of urination. First the bladder, second the urethra, and third the sphincter(s). The prostatic gland surrounds the urethra in the short segment between the bladder, at its outlet, and the external sphincter. When the patient experiences symptoms of bother which may be made manifest in several independent or co-existing difficulties during urination, treatment is often sought.

For example, bothersome symptoms might include: (i) incomplete emptying, (i.e., the patient is only able to urinate small volumes, e.g. <100 milliliters (ml), or has an elevated volume of urine left in the bladder following urination, e.g. >100 ml per attempt); (ii) experiencing frequent urges to urinate; (iii) intermittency (e.g. a patient's flow stops and starts often during urination); (iv) having a very weak and inconsistent urine flow stream; (v) stress incontinence (e.g. leaking during lifting or straining as a result of excessive urine in the bladder or weakened sphincters. With the exception of stress incontinence, each of these may contribute to nocturia (i.e., poor sleep due to the repeated need to urinate during the night), yet a further symptom.

Up to two million office visits annually in the United States are attributed to patients being bothered by some form of lower urinary tract symptoms (LUTS). As previously noted, there are three primary organs, and the prostate, involved with the event of urination. The symptoms are virtually always suspected to be caused by the intrusion of an enlarged prostate gland upon the urethra, however, symptoms are often caused by irregularities in bladder function, or sphincter deficiencies. For this reason, bladder outlet obstructions (BOO) is a major subgroup of LUTS. In men between the ages of 55 and 75 years, it is estimated that between 50 and 75% have some degree of bladder outlet obstruction, however, it may not be responsible for their symptoms.

Bladder outlet obstructions are primarily caused by the enlargement of the prostate gland (e.g., benign prostate hyperplasia (BHP)) which results in radial compression of the urethra surrounded thereby (i.e., the prostatic urethra), thus obstructing (i.e., constricting) urine flow, resulting in incomplete emptying of the bladder (i.e., there being what is clinically referred to as a "post void residual" (PVR) remaining in the bladder). Heretofore, males presenting with LUTS have few diagnostic options prior to either long term pharmacological, or invasive, irreversible, medical procedures such as trans urethral resection of the prostate (TURP), or non-surgical procedures such as thermal treatment of the prostate.

It is well known within the urological community that significant numbers of men undergoing treatment for prostate disease have sub-optimal results. According to Bruskewitz, benign prostatic hyperplasia (BPH) can be discussed in terms of prostatic enlargement, outlet obstruction and lower urinary tract symptoms (LUTS). Jepsen J. V. and Bruskewitz R. C., *Comprehensive Patient Evaluation for Benign Prostatic Hyperplasia,* 1998, Urology 51 (A4):13–18. In addition to the usual factors believed to lead to prostate induced LUTS (e.g., enlarged prostate and increased prostate muscle tone) other conditions of the lower urinary tract impact male voiding and need to be considered. Bruskewitz stated that a large part of the symptomotology of BPH might be explained by bladder dysfunction.

Bladder conditions that are prevalent in men with LUTS, either separately or in combination with outlet obstruction, include detrusor instability and detrusor hypocontractility. Kaplan S. A. and, Te A. E., *Uroflowmetry and Urodynamics,* 1995, Urologic Clinics of North America 22 (2):309–320. In a population of 787 men with symptoms of prostatism, Kaplan found that 504 (64%) had demonstrable prostatic urethral obstruction, of which 318 had concomitant detrusor instability. In the group, 181 had detrusor instability as their sole diagnosis. Impaired detrusor contractility was present in 134 (17%) and 49 of these had impaired detrusor contractility as their only diagnosis. Bruskewitz and others have also shown that a significant number of men with LUTS, including those who receive definitive treatment, are unobstructed. Abrams P., *In Support of Pressure Flow Studies for Evaluating Men with Lower Urinary Tract Symptoms,* 1994, Urology 44 (2): 153–55. Patient satisfaction rates after definitive prostate treatment vary from 100% to 75% or less. In some cases the lack of success may be related to unidentified bladder dysfunction. Bruskewitz concluded that bladder dysfunction should receive more attention (in the evaluation and treatment of LUTS) and better measures should be developed to quantify it. Presently, urodynamic methods to assess bladder outlet obstruction generally include uroflow testing, pressure flow testing and general patient history/examination.

Uroflow testing provides information about the combined contribution of the detrusor and urethra to uroflow. The limitation of uroflow testing is that it is not possible to determine with certainty in all cases whether a low flow and a poor voiding pattern are secondary to outlet obstruction, abnormal detrusor contractility or a combination thereof. Further, the test can be problematic because it is only a single event that can be influenced by patient factors such as anxiety and performance of the test (i.e. direction of the urine steam into the collecting reservoir). Abrams found that the success rate was only 70% when uroflow was used to select patients for surgery. Abrams P. H., *Prostatism and Prostatectomy: The Value of Flow Rate Measurement in the Preoperative Assessment for Operation.* J. Urol 1977, 177: 70–71.

Pressure flow testing can be used to define outlet obstruction and, in addition, provides information about the contractility and performance of the bladder. The pressure flow test, however, is not much more successful in predicting success of treatment, as defined by the patient, than uroflow (75% vs. 64%). Jepsen J. V. and Bruskewitz R. C., *Comprehensive Patient Evaluation for Benign Prostatic Hyperplasia,* 1998, Urology 51 (A4):13–18. Therefore the urological community as well as the Agency for Healthcare Policy & Research (AHCPR) do not find justification for its routine use.

Finally, the standard work-up of patients with LUTS being evaluated for bladder outlet obstruction generally consists of history and physical examination, including assessment of prostate volume, PSA, uroflow testing, quality of life, and symptom and bother index. Based on the results, treatment decision are made. Using these evaluations, underlying problems with bladder function cannot be detected.

In lieu of traditional urodynamic test methodologies such as the use of video urodynamics simultaneously with the holding and release of urine, cystometry, urethral pressure profiling, ultrasonic volume assessments (i.e., PVR), and uroflowmetry, each of which address the filing/emptying conditions (i.e., dynamics) of the bladder, endourethral devices and accompanying methodologies have been developed specifically to ascertain the nature of the BOO, see for example the disclosure of copending application Ser. Nos. 09/943,975, and 10/179,108, each of which are incorporated herein by reference. By permitting the structures of the lower urinary tract to physiologically act in a sequential and incremental manner upon portions of a device during a natural micturition event, an observable change in fluid dynamics in furtherance of lower urinary tract symptoms diagnosis may be noted.

Devices have been developed to be positioned in the urethra and/or bladder to correct the problems of obstruction and incontinence of urine flow. Heretofore known problems associated with endourethral devices, more particularly critical device components such as stents, valve actuators, flow conduits, etc., generally relate to, or are associated with, the physiology of the lower urinary tract (e.g., ingrowth, instability, pitting, depositions, etc.). Unappreciated or not fully appreciated relationships between the device and its environment have rendered heretofore known devices less effective at a minimum, and at a maximum, have been known to cause device component failure or render the device wholly ineffective, necessitating emergent removal and, as the case may be, urinary tract damage repair. Problems of device leakage, or less than complete emptying of the bladder are also widely known. Furthermore, issues surrounding device deployment and fit, positioning, repositioning, and retention (i.e., sufficient anchoring) have also been well documented.

It is especially critical that the endourethral device be stable with respect to position (i.e., a physiologically properly deployed and stable position), and comfortable to wear, as the urinary tract is sensitive to contact. Inter-urethral stents have been utilized within the male urethra within the prostatic region with many users foregoing such devices for alternate therapies due to feelings of discomfort and/or pain. Many endourethral devices have similarly been evaluated for urinary incontinence for females. Based upon clinical findings, many have been shown to be uncomfortable, thus severely retarding their utility as a therapy. Other devices have migrated into the bladder, or have been expelled under straining conditions.

Furthermore, it is imperative that the device be no more invasive than necessary. For instance, it is advantageous that the device minimally engage the structures of the lower urinary tract, particularly in accomplishing an anchoring function. For example, it is well known that secretions of the prostatic urethra, including the Cooper's gland, whether during sexual function or otherwise, is clinically beneficial, the secretions are comprised, in part, of antimicrobial agents which assist in the prevention of urinary tract infections. It is further believed that bathing of the bladder neck with urine assists infection prevention. Generally, flow of urine external of an endourethral device permits the free passage of urinary tract fluids from the urethra as urine is released, thereby allowing a more physiologically normal urine discharge. Thus, whether it be a short or long term endourethral device, for interventional, diagnostic or other purpose, stable anchoring in combination with physiologically proper, non-traumatic, fitted device deployment and retention is essential.

SUMMARY OF INVENTION

Embodiments of adjustable length endourethral devices intended for patients with Lower Urinary Tract Symptoms (LUTS) are provided. The subject devices are to be placed within the human urethra and in communication with the bladder. The devices of the subject invention are easily adjustable to accommodate the prostatic length and sphincteric anatomy of the patient. The devices are stabilized in the urethra at the bladder outlet, which prevents expulsion, and at the bulbous urethra, which prevents inward movement. For example, a first stabilizing structure of the device is preferably selectively and reversibly fluid filled, and positionable at the outlet of the bladder. A second stabilizing structure may be mechanical in nature, and is positionable at the bulbous urethra. The device stabilizing structures are selectively spaced apart by an element (i.e., a body) which selectively supports a portion of the urethra from closing without restricting the portion of the urethra in the region of the external sphincter. The devices of the subject invention provide for the regulation of the flow of urine from the bladder by the natural control of the external sphincter when the user desires, and do so utilizing device configurations which achieve a easy, secure, stable, fitted placement within the lower urinary tract.

The devices of the subject invention are easily placed into the patient without the necessity for external visualization such as rectal or abdominal ultrasound. Though these visualization methods are available to the urologist or physician, it is undesirable to use them because of cost and/or discomfort to the patient. The devices of all the embodiments may be installed in similar fashion to a Foley catheter by simply inserting the device, inflating the proximal anchor, withdrawing the device into the bladder outlet, and removing the insertion device.

Generally, the endourethral device includes proximal and distal anchor assemblies selectively spaced apart by a device body. The proximal anchor assembly is adapted to abuttingly engage at least portions of a bladder neck so as to at least proximally anchor said device, the distal anchor assembly being adapted to engage at least portions of a bulbous urethra so as to at least distally anchor said device. The body extends between the proximal and distal anchors, the device being adapted such that the anchors are selectively spaced apart for fixed positioning within a lower urinary tract in furtherance of a portion of the body at least partially traversing a prostatic urethra.

The foregoing and other objects, features, and advantages of the invention will be apparent with reference to the figures, the DETAILED DESCRIPTION OF THE INVENTION, and the claims herein after. The figures are not necessarily to dimensional or geometric scale, nor do they necessarily represent structures in accurate or representative relative scale. Emphasis rather is placed upon illustrating principals of the invention in a clear manner.

BRIEF DESCRIPTION OF THE DRAWINGS

FIG. 2 illustrates a further embodiment of the endourethral device of the subject invention, the body portions thereof having an alternate slidingly expanded and secured arrangement;

FIG. 3 illustrates yet a further embodiment of the endourethral device of the subject invention, the body portions thereof being in threaded engagement, and secured as FIG. 1A;

FIG. 5 depicts, in longitudinal section, yet a further embodiment of the endourethral device of the subject invention, more particularly the device body of FIG. 4 integral to a circumferential wall;

FIG. 5A illustrates the device of FIG. 5 secured in a longitudinally compressed condition with the retainer of FIG. 4A;

DETAILED DESCRIPTION OF THE DRAWINGS

Figure 1A:
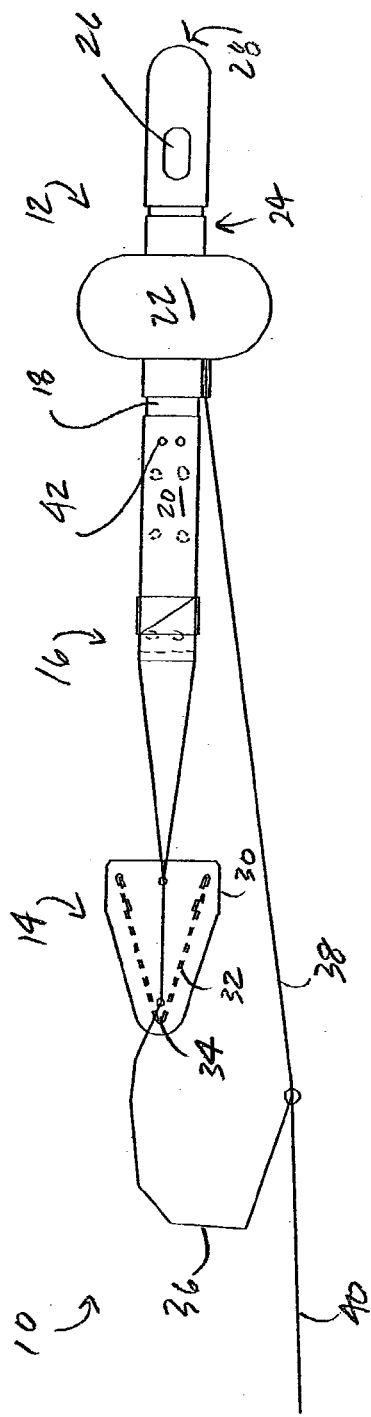
FIG. 1A illustrates the endourethral device of FIG. 1, the body thereof having a minimum length dimension (i.e., the body in a collapsed condition)

As a preliminary matter, Applicant's copending subject matter, application Ser. No. 10/059,100, incorporated herein by reference, is generally directed to devices especially suited for temporary, short term use as wearable urodynamic devices which allow patient initiated urination in men with lower urinary tract symptoms (LUTS), or symptoms of prostatism, so as to support open the prostatic urethra, thereby permitting temporarily relief or modification of symptoms, and discretionary clinician-patient collaborative monitoring and assessment of symptoms for the purpose of evaluating the contribution of the bladder and the bladder outlet to uroflow, urine voiding patterns and symptoms. The endourethral devices of the subject invention, in all embodiments, are likewise generally directed, and are further, particularly predicated upon the notion of easy, secure, stable, fitted placement within the lower urinary tract.

All embodiments of the endourethral device 10 of the subject invention generally include (FIG. 1B) a proximal anchor structure 12, a distal anchor structure 14, and a body 16 extending therebetween. The proximal anchor structure 12 is generally adapted to abuttingly engage at least portions of a bladder neck 11 so as to at least proximally anchor the device 10 whereas the distal anchor 14 is adapted to engage at least a portion of a bulbous urethra 13 so as to at least distally anchor the device. In addition to the anchor structures illustrated in the remaining figures and subsequently discussed, suitable anchor structures for the subject device are disclosed in copending application Ser. No. PCT/US01/24817, incorporated herein by reference, as well as the aforementioned application Ser. No. 10/059,100. Finally, it is further contemplated that such anchor structures may be readily modified, without undue experimentation, so as to include a variety of know retrieval mechanisms and/or structures, such as that disclosed in copending application Ser. No. 09/724,239, now U.S. Pat. No. 6,551,304 incorporated herein also by reference.

The device of the subject invention, in all its embodiments, is adapted such that the anchor structures are selectively spaced apart for positioning within the lower urinary tract in furtherance of a portion of the device body at least partially traversing the prostatic urethra. The alternate device body configurations for the subject endourethral device facilitate easy, secure, stable, placement within the lower urinary tract, and permit a physiological fitted placement of same.

Figure 1:
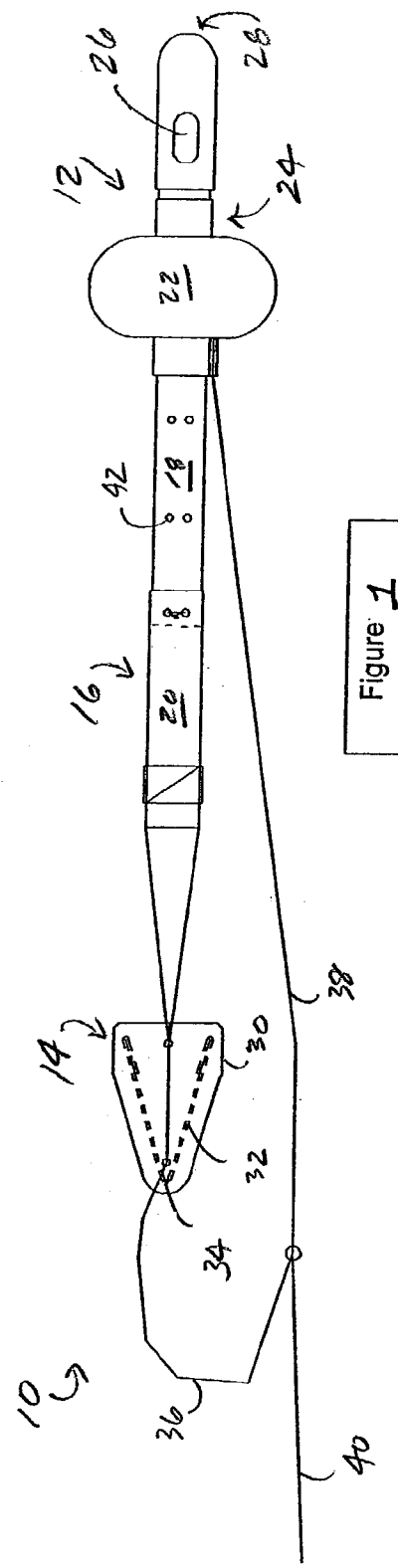
FIG. 1 illustrates a first embodiment of the endourethral device of the subject invention, the device having first and second body portions telescopingly affixed together.
Figure 1B:
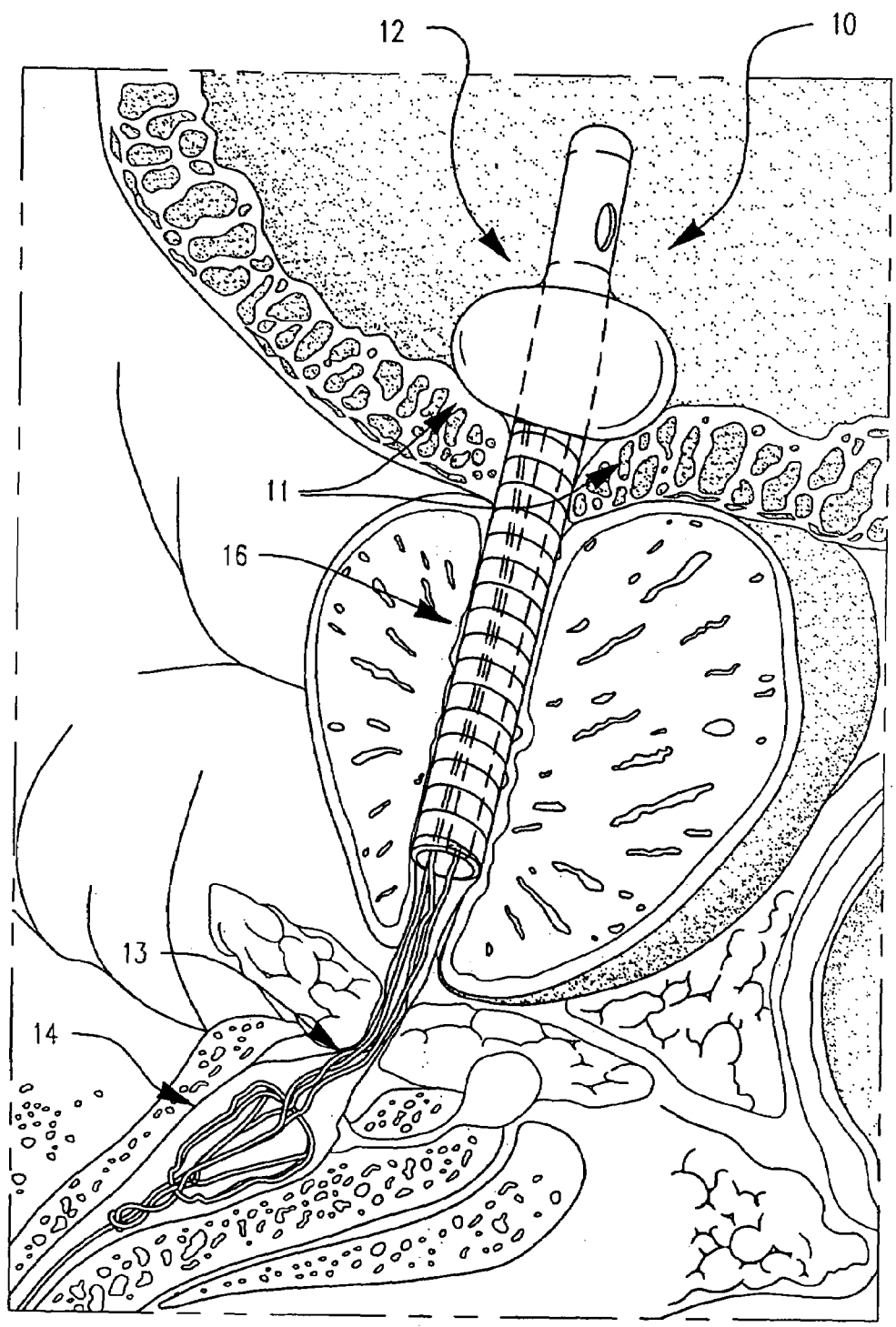
FIG. 1B generally illustrates a deployed or indwelling condition, within a lower urinary tract, of the device of the subject invention.

Generally referencing FIGS. 1 & 1A (see also FIGS. 2, 3, 4, 5, and 6 having reference numerals +200, +300, +400, +500, and +600 respectively for like structures), an endourethral device 10 is shown having proximal 12 and distal 14 anchor structures spaced apart by a device body 16. The device body 16 generally has proximal 18 and distal 20 segments, the body 16 being positionable within the lower urinary tract so as to at least partially traverse the prostatic urethra.

The proximal anchor structure 12, adapted to preferably abuttingly engage portions of the bladder neck so as to at least proximally anchor the device, is supported at least indirectly by the proximal segment 18 of the device body 16. The proximal anchor structure 12, as shown, includes at least a single bladder engaging element 22 radially extending from, and circumscribing, an anchor body 24. At least a single urine receiving aperture 26 is provided adjacent the proximal extremity 28 of the anchor body 24/device 10 so as to permit urine passage from the bladder and into the urethra. Optionally, multiple bladder engaging elements radially extend from the body of the proximal anchor such that urine is freely dischargable about or around an exterior surface of the anchor body so as to permit substantial bathing of the bladder neck and thereby realize the physiological benefits associated therewith.

The interface of the resilient bladder engaging elements relative to the anchor body (or proximal segment of device body), along with the methodology and structure (i.e., insertion/filling tool) for reversibly deploying such endourethral device, or devices of this style, is specifically disclosed in heretofore referenced copending application No. PCT/US01/24817, any modification or adaptation thereto to accommodate the structures of the contemplated endourethral device of the subject invention being considered within the skill of a person of ordinary skill in the art.

The distal anchor structure 14 is generally adapted to engage portions of the bulbous urethra so as to at least distally anchor the device, and is supported by at least a portion of the distal segment 20 of the device body 16. As shown, and preferably but not necessarily, the distal anchor structure 14 is mechanical in nature, generally including urethral engaging elements or portions 30 extending or depending therefrom, or otherwise integral thereto. The distal anchor structure 14 is of particularly low profile (i.e., an insubstantial hindrance to urine discharge), being reversibly expanded following deployment (e.g., by discharge from an insertion tool or the like). The mechanical anchor preferably tapers toward a distal end thereof, such configuration aiding the retrieval of the device.

The distal anchor structure 14 preferably, but not necessarily, includes a silicone encapsulated spring strut 32, or particular arrangement of struts or strut segments, either directly or indirectly extending from a central hub 34. When resiliently expanded, as for instance post deployment, the struts 32 expand to discretely engage portions of the urethral wall. A retrieval tether 36 is fixed to an extremity or end of the distal anchor assembly 14 to facilitate removal of the device generally, and is further joined to drain tether 38 and removal tether 40. The mechanics, functionality and structural details of the distal anchor assembly and tethering system are fully detailed in the aforementioned copending application, e.g., Ser. No. 10/059,100.

As previously noted, the device 10 is generally adapted such that the anchors 12, 14 are not fixedly positioned relative to each other, the device body 16 being longitudinally compactible. In the embodiments of FIGS. 1–3, the device body 16 includes proximal 18 and distal 20 portions, at least a segment of one of the portions being receivable within the other of the portions. The proximal body portion 18 is directly linked to the proximal anchor structure 12 whereas the distal body portion 20 is directly linked to the distal anchor structure 14. Each of the body components are generally tube-like and adapted to be selectively securable to each other. That is to say, the endourethral device comprises proximal and distal halves which are selectively and securable integratable, in coaxial fashion vis-a-vis union of the proximal and distal body portions, so as to have a patient specific physiological fit as could be determined by a urethral profiling device.

With specific reference to the embodiment of FIG. 1, the proximal body portion 18 is shown slidingly received within the distal body portion 20 in telescoping fashion. The distal body portion 20 (i.e., exterior tube) preferably includes at least a single pair of spaced apart apertures 42 in the wall thereof. The proximal body portion 18(i.e., interior tube) preferably includes spaced apart aperture pairs 42 registerable with the apertures in the proximal portion (compare FIG. 1 to FIG. 1A). The body portions 18, 20 are selectively secured to each other using suture, clips or other such structures or elements know to those of skill in the art. The preferred length range dimension for the device body 16 is from about 3 to 5.5 centimeters (cm) (i.e., the range of adjustability for the device is about 2.5 cm).

Referring now to the embodiment of FIG. 2, telescoping proximal 218 and distal 220 body portions of the device 210 are shown reversibly integrated via cooperation of a spring latch 246 and spring latch receiving structure 248. As shown, the exterior tube 220 is configured to include a spring latch 246, for instance an elongate deflectable arm 250 having an interiorly extending protrusion (i.e., knob) 252. A series of spaced apart knob receiving apertures 248 pass through the wall of the interior tube 218, a portion of the spring latch 246, namely the knob 252, being reversibly and selectively receivable in any one of same for securing the proximal 218 and distal 220 body portions relative to each other. The preferred length range dimension for the device body 216 is from about 3 to 5.5 centimeters (cm) (i.e., the range of adjustability for the device is about 2.5 cm).

Referring now to the embodiment of FIG. 3, cooperative engagement of the body portions is achieved via threaded engagement of same. As shown, the proximal body portion 318 includes a male thread configuration with the distal body 320 portion including a female thread configuration. As may be readily appreciated, upon union of the threaded elements, the device 310 of the subject embodiment is longitudinally compactable/expandable. As with the embodiment of FIG. 1, the body portions are selectively securable via registration and affixation of apertures 342 in the respective walls of the body portions. Affixation of the body elements of the subject embodiment may suitable be accomplished using a locking nut (not shown) receivable on the proximal body portion, such arrangement providing greater freedom in adjustability. The preferred length range dimension for the device body 316 is from about 3 to 5.5 centimeters (cm) (i.e., the range of adjustability for the device is about 2.5 cm).

Figure 4:
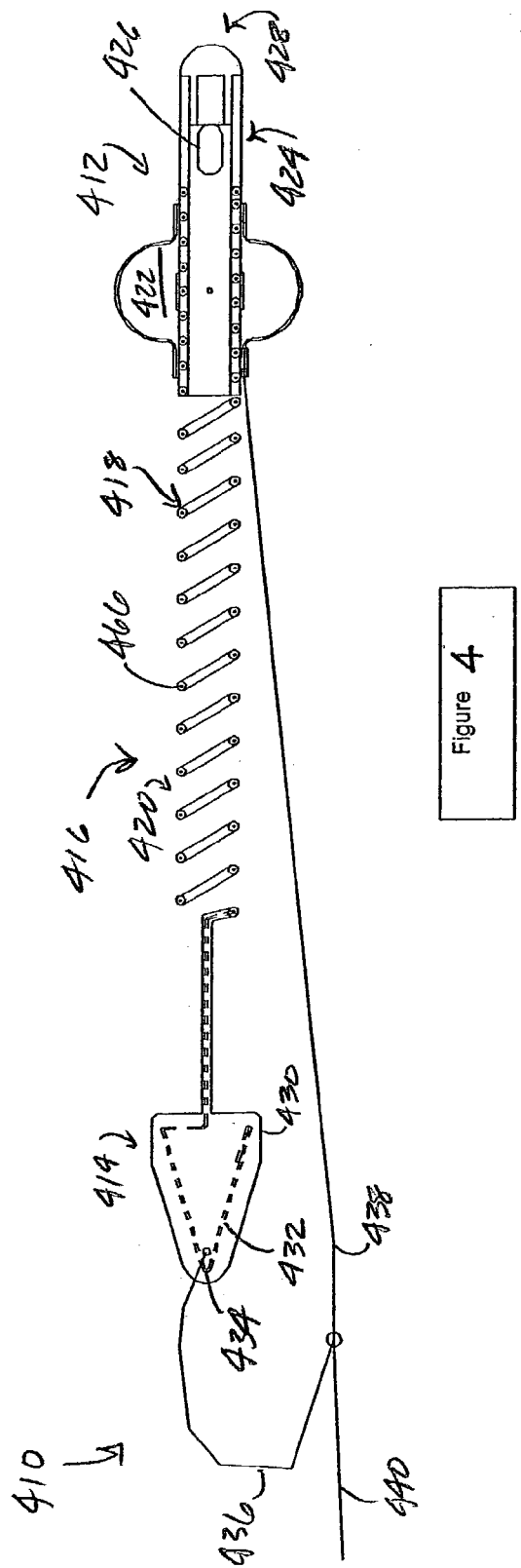
FIG. 4 depicts, in longitudinal section, yet a further embodiment of the endourethral device of the subject invention, the body thereof being longitudinally compressible.

Referring now to FIGS. 4 & 5, an endourethral device 410, 510 is shown having a continuous construction throughout its length, a device body 416, 516 being nonetheless interposed between proximal 412, 512 and distal 414, 514 anchoring structures. The device body 416, 516 generally includes a cylindrically, or otherwise as the case may be, coiled coated wire 466, 566. Alternately and suitably, the device body may comprise other known longitudinally compressible configurations (e.g., serpentine). The body may be "open" throughout its length (FIG. 4/4A) or be "closed" throughout at least a portion of its length (FIG. 5/5A), that is to say, body 516 may include a circumferential wall 568, wire 566 being integral thereto. The device bodies 416, 516 of FIGS. 4 and 5 are shown in a static, normally extended condition.

Figure 4A:
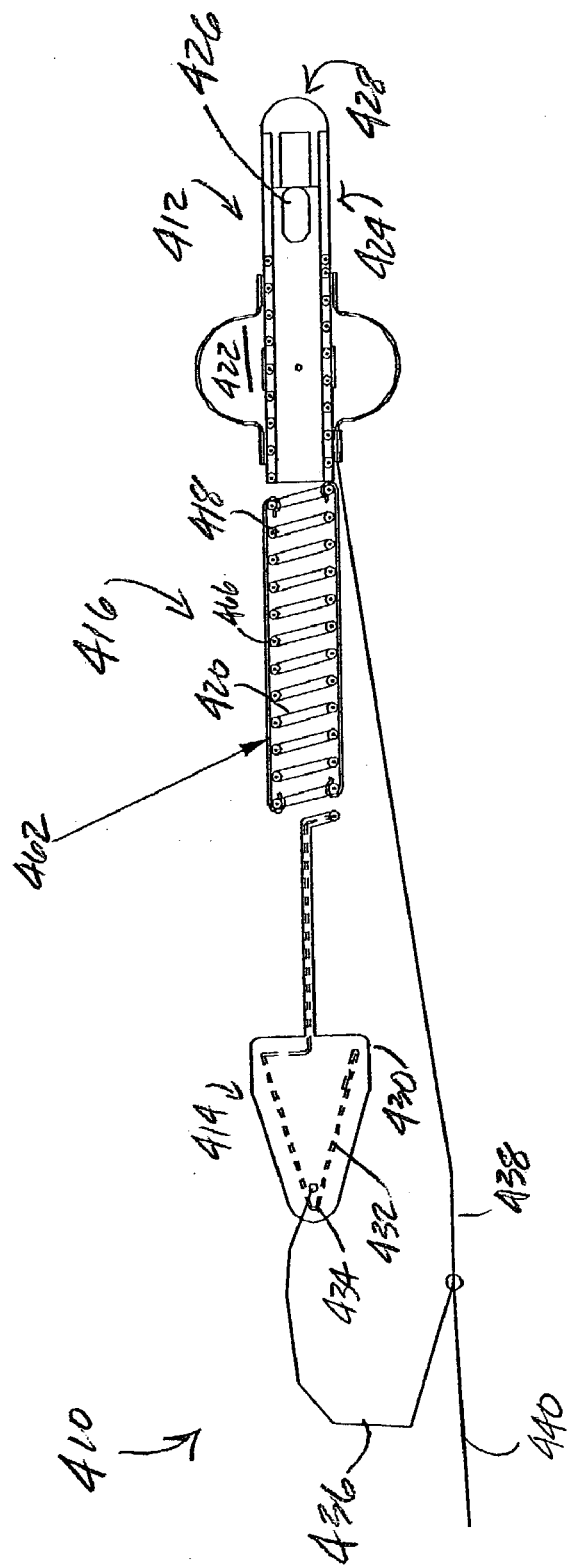
FIG. 4A illustrates the device of FIG. 4 secured in a longitudinally compressed condition with a retainer.

Referring now specifically to FIGS. 4/4A and 5/5A, the endourethral device includes a longitudinally compactable body 416, 516, more particularly a longitudinally compressible body. Selective, secure adjustment is achieved via receipt of at least a single retainer 462, 562 (e.g., a clip) on at least a portion of the longitudinally compressed device body 416, 516 (FIGS. 4A & 5A). The retaining clip 462, 562 is preferably configured such that its opposing ends securingly receive a coil portion (i.e., a single coil winding) of the device body 462, 562. As is readily appreciated with reference to the figures, a plurality of length dimensions are achievable for body 416, 516 using a retainer of fixed dimension, the number of coil windings captured by the retainer being length determinative. Furthermore, retainers of varying length may be suitably supplied for application to the body should pitch maintenance, or other coil character/quality, sought to be maintained. For the embodiment of FIG. 5, an aperture or series of apertures 564 are preferably, but not necessarily, provided through the body wall 568 to facilitate secure placement of the retainer 562 with respect to the device body 516.

Figure 6A:
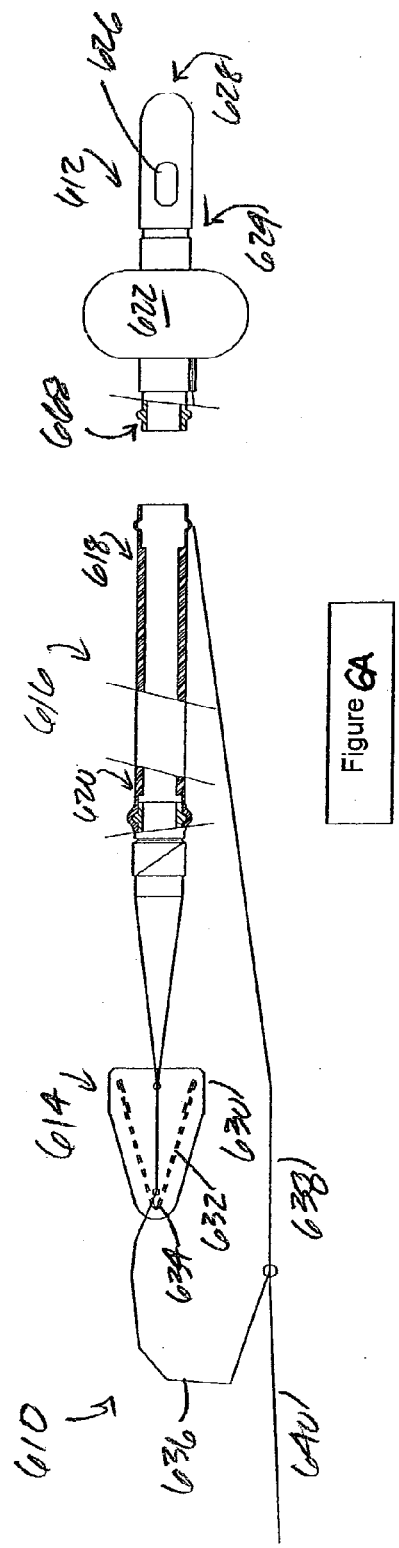
FIG. 6 depicts, in partial longitudinal section, yet a further embodiment of the endourethral device of the subject invention, more particularly, the integration of a substitutable, variable length body portion with and to the anchor assemblies; and, FIG. 6A illustrates the device of FIG. 6 in a partially disassembled condition.
Figure 6:
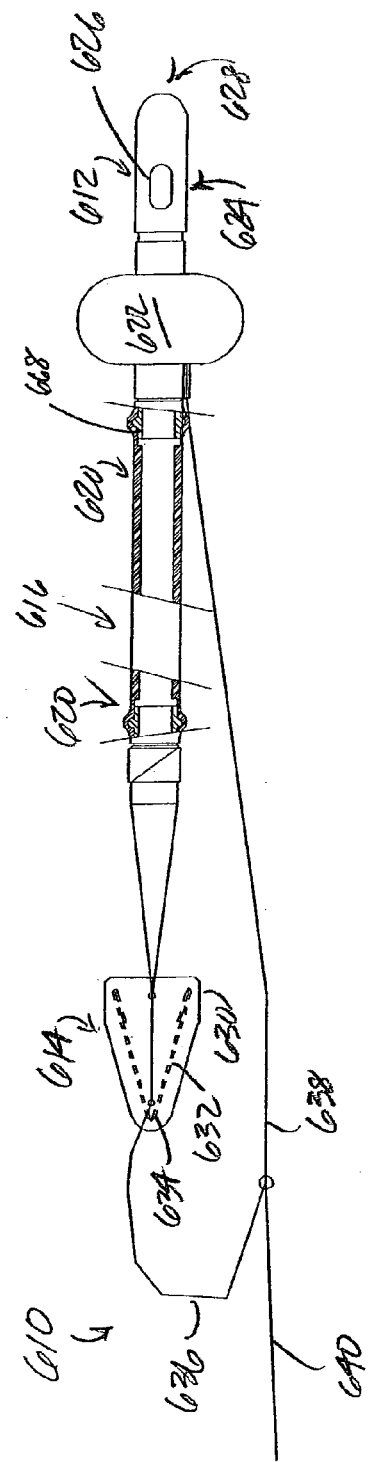

Referring now to FIGS. 6 & 6A, there is shown an endourethral device 610 having a body portion 616 interposed between proximal 612 and distal 614 anchor assemblies, the device being adapted such that it is variably dimensionable. More particularly, opposing ends of the device body 616 are configured to reversibly receive the anchor assemblies 616, 614 (i.e., the proximal portion 618 of the body 616 mates with the proximal anchor structure 612 whereas the distal portion 620 of the body 616 mates with the distal anchor structure 614). As shown, the anchor structures 612, 614 include a profiled end 668 (i.e., an end configured so as to include a "male" fitting) which is interlockingly received into each of the profiled opposing ends of the device body 616 (i.e., the opposing ends of the device body are configured so as to include a "female" fitting). The arrangement of the aforementioned structures may be readily varied while accomplishing the desired reversible interlocking device assembly. Furthermore, alternate interlocking mechanisms, such as via a bayonet connection, threaded connection or barbed connection, etc. may be utilized without departing from the scope of the present invention.

Advantageously, a device body 616 is selectively integrated with stock or standard anchoring structures 612, 614 for insertion and positioning based upon urethral profiling, as for instance by utilizing diagnostic urethral assemblies as disclosed in copending application Ser. No. 09/943,975 now U.S. Pat. No. 6,719,709 and Ser. No. 10/179,108. Having delimited the dimensional landmarks of the lower urinary tract, more particularly the prosthetic urethra, an appropriately dimensioned device body may be equipped with the anchor structures show, or disclosed in the references incorporated by reference. The body lengths preferably range from about 2–7 cm, the "finished" device for deployment being from about 4–9 cm. The interlocking feature provides a minimum attachment force of about 3 lbf for securing the linkage.

This invention disclosure provides device configurations which achieve a easy, secure, stable, fitted placement within the lower urinary tract. There are other variations of this invention which will become obvious to those skilled in the art. It will be understood that this disclosure, in many respects, is only illustrative. Changes may be made in details, particularly in matters of shape, size, material, and arrangement of parts without exceeding the scope of the invention. This is particularly the case, for example, with the specific features of each of the device body portions which facilitate the cooperative engagement of same in furtherance of selectively spacing apart the anchor structures so as to provided a fitted placement. Accordingly, the scope of the invention is as defined in the language of the appended claim. As will further be appreciated, it is contemplated that the disclosed features permitting fitted placement, and their equivalents, are likewise contemplated and hereby embraced for application regarding known endourethral devices for diagnosis, managing or treating urological disorders, the benefits thereby accruing thusly being available generally to patient's presenting with such disorders.

What is claimed is:

1. An endourethral device comprising:
   a. a proximal anchor structure adapted to abuttingly engage at least portions of a bladder neck so as to at least proximally anchor said device;
   b. a distal anchor structure adapted to engage at least portions of a bulbous urethra so as to at least distally anchor said device; and,
   c. a variably dimensionable body extending between said proximal and said distal anchors, said body comprising a proximal portion and a distal portion, at least a segment of one of said portions being receivable within the other of said portions, one of said body portions including a single aperture pair registerable with spaced apart aperture pairs of the other of said body portions for fixed positioning within a lower urinary tract in furtherance of a portion of said body at least partially traversing a prostatic urethra.

2. The endourethral device of claim 1 wherein said distal anchor structure is spaced apart from said distal body portion by about 2–4 cm via a linkage.

3. An endourethral device comprising:
   a. a proximal anchor structure adapted to abuttingly engage at least portions of a bladder neck so as to at least proximally anchor said device;
   b. a distal anchor structure adapted to engage at least portions of a bulbous urethra so as to at least distally anchor said device;
   c. a variably dimensionable body extending between said proximal and said distal anchors, said body comprising a proximal portion and a distal portion, at least a segment of one of said portions being receivable within the other of said portions, said body portions being selectively securable to each other, one of said body portions being threadingly received upon a portion of the other of said body portions; and,
   d. means for reversibly securing said proximal and said distal body portions, said device being adapted such that said anchors are selectively spaced apart for fixed positioning within a lower urinary tract in furtherance of a portion of said body at least partially traversing a prostatic urethra.

4. The endourethral device of claim 3 wherein one of said body portions includes a single aperture pair registerable with spaced apart aperture pairs of the other of said body portions.

5. The endourethral device of claim 3 wherein said distal anchor structure is spaced apart from said distal body portion by about 2–4 cm via a linkage.

6. An endourethral device comprising:
   a. a proximal anchor structure adapted to abuttingly engage at least portions of a bladder neck so as to at least proximally anchor said device;
   b. a distal anchor structure adapted to engage at least portions of a bulbous urethra so as to at least distally anchor said device;
   c. a variably dimensionable, longitudinally compressible body extending between said proximal and said distal anchors, said body comprising a coil spring; and,
   d. a spring clip, said spring clip retaining a plurality of select coils of said coil spring between opposing ends thereof such that said anchors are selectively spaced apart for fixed positioning within a lower urinary tract in furtherance of a portion of said body at least partially traversing a prostatic urethra.

7. An endourethral device comprising:
   a. a proximal anchor structure adapted to abuttingly engage at least portions of a bladder neck so as to at least proximally anchor said device;
   b. a distal anchor structure adapted to engage at least portions of a bulbous urethra so as to at least distally anchor said device; and,
   c. a body extending between said proximal and said distal anchors, said body being reversibly detachable from said anchors, variably dimensioned bodies being readily substituted therefore, said device being adapted such that said anchors are selectively spaced apart for fixed positioning within a lower urinary tract in furtherance of a portion of said body at least partially traversing a prostatic urethra.

8. An endourethral device comprising an anchor for securing a proximal portion of said device at a bladder neck, a coil extending from said anchor, and means for selectively retaining said coil in a less than fully extended condition, at least a portion of said coil traversing a prostatic urethra.

9. An endourethral device comprising a proximal anchor structure adapted to abuttingly engage at least portions of a bladder neck so as to at least proximally anchor said device, a selectively dimensionable body extending from said proximal anchor, and a distal anchor structure tethered to said body for engagement with a bulbous urethra.

10. The endourethral device of claim 9 wherein said body is longitudinally compactable.

11. The endourethral device of claim 10 wherein said body includes proximal and distal portions.

12. The endourethral device of claim 11 wherein said portions of said body are adapted for cooperative engagement.

13. The endourethral device of claim 11 wherein said portions of said body are selectively securable to each other.

14. The endourethral device of claim 9 wherein said distal anchor structure is spaced apart from said body by about 2–4 cm via a linkage.

15. An endourethral device comprising:
   a. a proximal anchor structure adapted to abuttingly engage at least portions of a bladder neck so as to at least proximally anchor said device;
   b. a distal anchor structure adapted to engage at least portions of a bulbous urethra so as to at least distally anchor said device; and,
   c. a selectively dimensionable body for fixed extension between said proximal and said distal anchors, said body including a segment adapted to permit physiological external sphincter function, said distal anchor structure being spaced apart from said body by about 2–4 cm via a linkage.

* * * * *